US008871549B2

(12) United States Patent
Ellis-Monaghan et al.

(10) Patent No.: US 8,871,549 B2
(45) Date of Patent: Oct. 28, 2014

(54) BIOLOGICAL AND CHEMICAL SENSORS

(71) Applicant: International Business Machines Corporation, Armonk, NY (US)

(72) Inventors: John J. Ellis-Monaghan, Grand Isle, VT (US); Jeffrey P. Gambino, Westford, VT (US); Derrick Liu, Winooski, VT (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/767,024

(22) Filed: Feb. 14, 2013

(65) Prior Publication Data

US 2014/0225166 A1     Aug. 14, 2014

(51) Int. Cl.
*H01L 21/00* (2006.01)
*H01L 29/66* (2006.01)
*G01N 27/414* (2006.01)

(52) U.S. Cl.
CPC ........ *G01N 27/414* (2013.01); *H01L 29/66477* (2013.01)
USPC .................................. 438/49; 438/5; 257/253

(58) Field of Classification Search
CPC ..................... H01L 23/53238; H01L 27/0207; G01N 27/414; G01N 33/487
USPC ................. 438/49, 5; 257/253, 414; 204/409; 216/19, 39
See application file for complete search history.

(56) References Cited

U.S. PATENT DOCUMENTS

| | | | |
|---|---|---|---|
| 4,636,827 A * | 1/1987 | Rudolf | 257/253 |
| 5,407,854 A * | 4/1995 | Baxter et al. | 438/49 |
| 5,693,577 A | 12/1997 | Krenik et al. | |
| 5,777,372 A | 7/1998 | Kobashi | |
| 6,024,924 A | 2/2000 | Schoning et al. | |
| 6,870,235 B2 | 3/2005 | Abstreiter et al. | |
| 6,914,279 B2 | 7/2005 | Lu et al. | |
| 7,361,946 B2 * | 4/2008 | Johnson et al. | 257/253 |
| 7,521,280 B1 * | 4/2009 | Anderson et al. | 438/72 |
| 7,948,015 B2 | 5/2011 | Rothberg et al. | |
| 2004/0007740 A1 | 1/2004 | Abstreiter et al. | |
| 2004/0063304 A1 | 4/2004 | Hagen et al. | |
| 2008/0223794 A1 | 9/2008 | Yamamichi et al. | |
| 2009/0243584 A1 | 10/2009 | Zhang et al. | |
| 2010/0248209 A1 * | 9/2010 | Datta et al. | 435/5 |
| 2013/0157436 A1 * | 6/2013 | Hummler | 438/424 |

OTHER PUBLICATIONS

M. J. Milgrew et al., "Matching the Transconductance Characteristics of CMOS ISFET Arrays by Removing Trapped Charge," IEEE Transactions on Electron Devices, vol. 55, Issue 4, Apr. 2008, pp. 1074-1079.
M. J. Schoning et al., "Silicon-based field-effect devices for (bio-)chemical sensing," International Conference on Advanced Semiconductor Devices and Microsystems, ASDAM 2008. Oct. 12-16, 2008, pp. 31-38.
H. S. Yang et al., "A 3D interconnect system for large biosensor array and CMOS signal-processing IC integration," 2010 International Interconnect Technology Conference (IITC), Jun. 6-9, 2010, 3 pages.

* cited by examiner

*Primary Examiner* — Caridad Everhart
(74) *Attorney, Agent, or Firm* — Wood, Herron & Evans LLP; Anthony J. Canale

(57) ABSTRACT

Device structures, fabrication methods, and design structures for a biological and chemical sensor used to detect a property of a substance. The device structure includes a drain and a source of a field effect transistor formed at a frontside of a substrate. A sensing layer is formed at a backside of the substrate. The sensing layer is configured to receive the substance.

26 Claims, 6 Drawing Sheets

BIOLOGICAL AND CHEMICAL SENSORS

BACKGROUND

The invention generally relates to semiconductor manufacturing and, more particularly, to device structures, fabrication methods, and design structures for a biological or chemical sensor.

Biological and chemical sensors based on ion-sensitive field effect transistors (ISFET) can be integrated with modern microelectronic devices and used to detect and measure various aspects of chemical reactions and substance properties. For example, an ion-sensitive field effect transistor (ISFET) may be used to measure ion concentrations, such as hydrogen ion concentration, in a sample of an analyte. An ISFET is similar to a metal oxide semiconductor field effect transistor (MOSFET), but lacks a gate electrode. Instead, an ion-sensitive membrane is placed over the channel region of the ISFET and is exposed to the analyte sample. A reference electrode of the ISFET is separated from the ion-sensitive membrane by the solution. The potential difference between the channel and the reference electrode is a function of the ion concentration in the analyte sample. An operating characteristic of the ISFET may be measured and used to calculate ion concentration.

Improved device structures, fabrication methods, and design structures for a biological and chemical sensor are needed.

BRIEF SUMMARY

In an embodiment of the invention, a method is provided for forming a sensor to detect a property of a substance. The method includes forming a drain and a source of a field effect transistor at a frontside of a substrate, and forming a sensing layer at a backside of the substrate opposite from the frontside of the substrate. The sensing layer is configured to receive the substance.

In an embodiment of the invention, a device structure is provided for a sensor used to detect a property of a substance. The device structure is formed using a substrate having a frontside and a backside opposite from the frontside. The device structure includes a field effect transistor with a drain and a source at the frontside of the substrate, and a sensing layer at the backside of the substrate. The sensing layer is configured to receive the substance.

In an embodiment of the invention, a hardware description language (HDL) design structure is encoded on a machine-readable data storage medium. The HDL design structure comprises elements that, when processed in a computer-aided design system, generates a machine-executable representation of a device structure for a provided for a sensor used to detect a property of a substance. The HDL design structure includes a field effect transistor with a drain and a source at a frontside of a substrate, and a sensing layer at a backside of the substrate opposite from the frontside of the substrate. The sensing layer is configured to receive the substance. The HDL design structure may comprise a netlist. The HDL design structure may also reside on storage medium as a data format used for the exchange of layout data of integrated circuits. The HDL design structure may reside in a programmable gate array.

BRIEF DESCRIPTION OF THE SEVERAL VIEWS OF THE DRAWINGS

The accompanying drawings, which are incorporated in and constitute a part of this specification, illustrate various embodiments of the invention and, together with a general description of the invention given above and the detailed description of the embodiments given below, serve to explain the embodiments of the invention. In the drawings, like reference numerals refer to like features.

DETAILED DESCRIPTION

Figure 1:
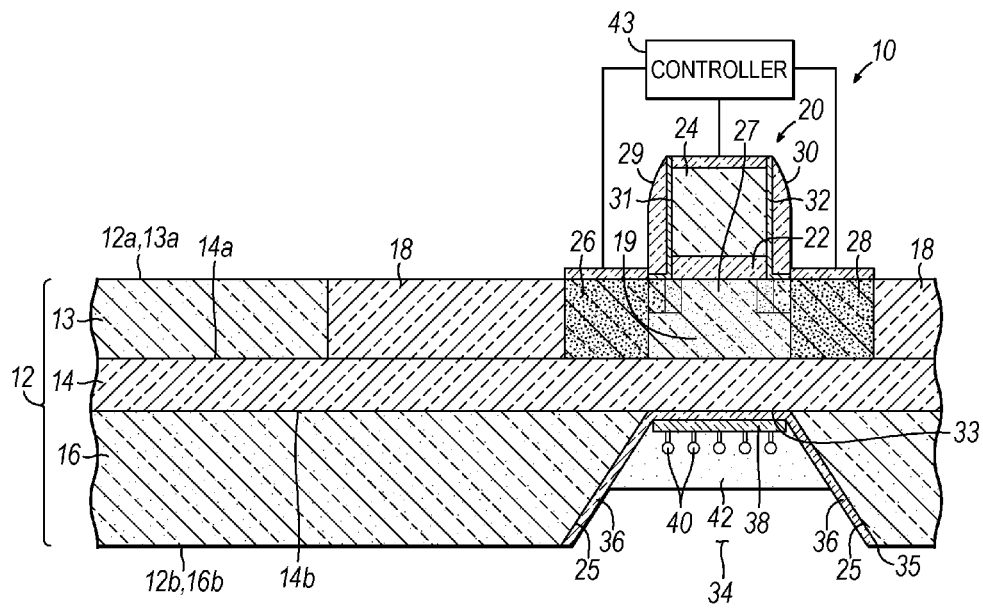
FIGS. 1-6 are cross-sectional views of biological and chemical ion sensors in accordance with embodiments of the invention.

With reference to FIG. 1 and in accordance with an embodiment of the invention, a sensor, which is generally indicated by reference numeral 10, is formed using a semiconductor substrate 12. The substrate 12 may be semiconductor-on-insulator (SOI) wafer that includes a device layer 13, a buried insulator layer 14, and a handle wafer 16. The device layer 13 is separated from the handle wafer 16 by the intervening buried insulator layer 14 and is in direct contact along a planar interface with a top surface of the buried insulator layer 14. The buried insulator layer 14 electrically insulates the handle wafer 16 from the device layer 13, which is considerably thinner than the handle wafer 16.

Before processing, a top surface 13a of the device layer 13 defines a top surface or frontside 12a of the substrate 12 and a bottom surface 16b of the handle wafer 16 defines a bottom surface or backside 12b of the substrate 12. The frontside 12a of the substrate 12 is opposite from the backside 12b of the substrate 12 in that the thickness of the substrate 12 intervenes. During the process flow described herein, the backside 12b of the substrate 12 may be modified so that the bottom surface 16b and the backside 12b are no longer coincident. For example, the backside 12b of the substrate 12 may be modified to define a recess in the handle wafer 16 (as depicted in the representative embodiment of FIG. 1) or to remove the handle wafer 16 in its entirety so that the bottom surface 14b of buried insulator layer 14 either partially or entirely assumes the role of substrate backside. The thickness of the handle wafer 16 may also be reduced from its original thickness by grinding, polishing, etching, etc.

The buried insulator layer 14 may be comprised of an electrical insulator and, in particular, may be comprised of silicon dioxide (e.g., $SiO_2$) to constitute a buried oxide layer. The device layer 13 and handle wafer 16 may each be comprised of a monocrystalline semiconductor material, such as single crystal silicon or another crystalline semiconductor material that contains primarily silicon, and the semiconductor material of the device layer 13 may be device quality. The SOI substrate 12 may be fabricated by any suitable conventional technique, such as wafer bonding techniques or separation by implantation of oxygen (SIMOX) techniques, familiar to a person having ordinary skill in the art.

Trench isolation regions 18 may be formed that circumscribe and electrically isolate a portion of the device layer 13 to define a device region 19 for the sensor 10. The trench isolation regions 18 may be isolation structures formed by a shallow trench isolation (STI) technique that relies on a lithography and dry etching process to define closed-bottomed trenches that may land on the top surface 14a of the buried insulator layer 14, deposit an electrical insulator to fill the trenches, and planarize the electrical insulator relative to the front surface defining the frontside 12a of the substrate 12 using a chemical mechanical polishing (CMP) process. The electrical insulator may be comprised of an oxide of silicon, such as densified tetraethylorthosilicate (TEOS) deposited by chemical vapor deposition (CVD).

A field effect transistor 20 of the sensor 10 is formed using the device region 19 of the device layer 13 of substrate 12. The field effect transistor 20 includes a dielectric layer 22 and a gate electrode 24 that are positioned on a top surface 12a of the device layer 13 with the dielectric layer 22 positioned between the gate electrode 24 and the device layer 13. The conductor constituting the gate electrode may comprise, for example, metal, silicide, polycrystalline silicon (polysilicon), or any other appropriate material(s) deposited by a CVD process, etc. The gate dielectric layer may be comprised of any suitable dielectric or insulating material including, but not limited to, silicon dioxide, silicon oxynitride, a high-k dielectric material such as hafnium oxide or hafnium oxynitride, or layered combinations of these dielectric materials.

The dielectric layer 22 and gate electrode 24 may be formed in the device region 19 by serially forming additive layers of the constituent dielectric material and conductor on the top surface of the device layer 13. The material of dielectric layer 22 may be deposited by atomic layer deposition (ALD), CVD, etc. The material of the gate electrode 24 may be deposited by CVD, ALD, physical vapor deposition (PVD), etc. The additive layers may be lithographically patterned using lithography and etching processes to define the dielectric layer 22 and gate electrode 24. To that end, a resist (not shown) is applied by a spin coating process, pre-baked, exposed to radiation projected through a photomask, baked after exposure, and developed with a chemical developer to form a mask that includes an island coinciding spatially with the intended location of the dielectric layer 22 and gate electrode 24. The pattern is transferred from the mask to the additive layers with a wet etching process or dry etching process, such as a reactive-ion etching (RIE) or a plasma etching process, that removed dielectric material and conductor that are unprotected by the mask island. The etching process may rely on an etchant chemistry that removes the additive materials selective to (i.e., at a higher etch rate than) the material constituting the buried insulator layer 14. The resist may be removed by ashing or solvent stripping and a conventional cleaning process may be applied to remove contaminants.

A source 26 and a drain 28 of the field effect transistor 20 may be formed in the device region 19 by, depending on the type of device being formed, implanting ions of a suitable n-type dopant from Group V of the Periodic Table (e.g., phosphorus, arsenic or antimony), or a suitable p-type dopant selected from Group III of the Periodic Table (e.g., boron or indium) into the device layer 13. The dopant introduction may use the gate electrode 24 as a self-aligning mask during ion implantation and electrically activated by an annealing step. A channel 27 is defined in the device layer 13 between the source 26 and drain 28. The field effect transistor 20 may include other components such as halo regions, lightly doped drain (LDD) regions, etc. in the device layer 13. Non-conductive spacers 29, 30 and non-conductive spacers 31, 32 may be formed on the exterior sidewalls of the dielectric layer 22 and gate electrode 24.

After the field effect transistor 20 is fabricated by complementary metal-oxide-semiconductor (CMOS) processes, the substrate 12 is thinned by grinding and/or polishing the handle wafer 16. A recess, generally indicated by reference numeral 34, is formed in the thinned handle wafer 16 at the backside 12b of the substrate 12. The recess 34 has an unconcluded opening 35 at its mouth and a base surface 33, and may have an inclined sidewall 25 that connects the opening 35 with the base surface 33. The sidewall 25 is tapered to diverge with increasing distance from the base surface 33. In the representative embodiment, the base surface 33 is coextensive with the buried insulator layer 14. The backside 12b of substrate 12 is coextensive with the sidewall 25 and base surface 33 of the recess 34, as well as the bottom surface 16b of handle wafer 16.

The recess 34 may be defined in the handle wafer 16 and, hence, the backside 12b of the substrate 12 using a photolithography process and an etching process. To that end, a mask layer (not shown) may be applied on the handle wafer 16. The mask layer may comprise a photoresist that is applied as a layer by a spin coating process, pre-baked, exposed to radiation projected through a photomask, baked after exposure, and developed with a chemical developer to form an etch mask that includes a pattern of openings coinciding with the intended location of recess 34. The opening is transferred from the mask layer to the handle wafer 16. The etching process may comprise a wet etching process or a dry etching process, such as reactive-ion etching (RIE), having an appropriate etch chemistry. The mask layer is removed after the recess 34 is formed. If comprised of a photoresist, the mask layer may then be removed by ashing or solvent stripping, followed by a conventional cleaning process.

An insulator layer 36 comprised of a dielectric material, such as an electrical insulator like $Si_3N_4$, may be applied to the recess 34 as a liner. The insulator layer 36 may be patterned using a photolithography process and an etching process as depicted in the representative embodiment, or may alternatively be unpatterned at least locally to the recess 34. In an alternative embodiment, the insulating layer 34 may be omitted.

A sensing layer 38 is applied to the insulator layer 36 (or the bottom surface 14b of the buried insulator layer 14 if the insulator layer 36 is absent) and patterned to define an electrode with a sensing area inside the recess 34 on the base surface 33 and at the backside 12b of the substrate 12. The sensing layer 38 is comprised of a conductive material, such as an alloy comprising gold and titanium (Ti/Au). The sensing layer 38 may be patterned using a photolithography process and an etching process to localize the sensing layer 38 within the recess 34. A mask layer (not shown) may be applied on the handle wafer 16 for patterning the sensing layer 38. The mask layer may comprise a photoresist that is applied as a layer by a spin coating process, pre-baked, exposed to radiation projected through a photomask, baked after exposure, and developed with a chemical developer to form an etch mask that includes an island coinciding with the intended location of sensing layer 38 inside the recess 34. The island is transferred from the mask layer to the sensing layer 38. The etching process may comprise a wet etching process or a dry etching process, such as reactive-ion etching (RIE), having an appropriate etch chemistry. The mask layer is removed after the sensing layer 38 is patterned. If comprised of a photoresist, the mask layer may then be removed by ashing or solvent stripping, followed by a conventional cleaning process.

The sensing layer 38 may further comprise a chemical or biological recognition element 40. The recognition element 40 may include molecular receptors configured to bind with a biological or chemical species contained in a substance, such as a liquid, fluid, or gas, that is present as an analyte sample 42 inside the recess 34. In one embodiment, the recognition element 40 may comprise an enzyme that produces a measureable chemical reaction in response to the presence of the analyte sample 42. The analyte sample 42 comprises a small reaction volume of a substance is supplied to the sensing layer 38. The sample 42 may be in the form of a solution, a liquid, a fluid, a gas, etc. The recognition element 40 may be fixed in whole or in part with a static location on the sensing layer 38. The sensing layer 38 and recognition element 40 are located on an opposite surface 14b of the buried insulator layer 14 from the field effect transistor 20.

In operation, the analyte sample 42 is supplied to the recess 34 in proximity to the sensing layer 38 of the sensor 10. The recess 34 may function as a reaction chamber or well of the sensor 10. As examples, the sample 42 may be intentionally introduced in an analysis system to which the sensor 10 is coupled or may result from sampling a stream of the fluid or gas in a detection system to which the sensor 10 is coupled. With the sample 42 present in the recess 34, current is forced through the channel 27 in the device layer 13 between the source 26 and drain 28 of the field effect transistor 20. The threshold voltage of the field effect transistor 20 is affected by the specific binding of target molecules in the sample 42 to the recognition element 40 on the sensing layer 38. For example, charged target molecules in the sample 42 may bind to the molecular receptors of the recognition element 40 of the sensor 10.

The threshold voltage, which appears as a potential on the gate electrode 24 of the field effect transistor 20, resulting from a particular sample 42 may be measured and compared with the threshold voltage in the absence of a sample or with threshold voltages for standards generated with samples of known concentration of the target molecule. A single threshold voltage may be measured or, alternatively, a time series of threshold voltages may be measured. For example, multiple measures may be applied to track the progress of a chemical reaction occurring in the sample 42 while resident in the recess 34 and on the sensing layer 38. The chemical reaction may modulate the ion charge in the sample 42 and, as a result, modulate the current between the source 26 and drain 28 to provide a time dependence.

A controller 43 may be coupled with the sensor 10 and, in particular, with the field effect transistor 20. The controller 43 may include a memory and at least one processor coupled to the memory. The controller 43 may operate under the control of an operating system and execute, or otherwise rely upon, various computer software applications, components, programs, objects, modules, data structures, etc. At least one of these applications, when executed, generally causes the controller 43 to operate the sensor 10 and to process analog measurements received from the sensor 10. For interface with a user or operator, the controller 43 may further include a user interface incorporating one or more user input/output devices, e.g., a keyboard, a pointing device, a display, a printer, etc. and may be coupled over a network interface coupled with a communication network. The controller 43 also may be in communication with one or more mass storage devices, which may be internal hard disk storage devices, external hard disk storage devices, external databases, storage area network devices, etc.

The sensor 10 may be employed to detect and measure concentrations/levels of hydrogen ions, other types of ions, non-ionic molecules or compounds, binding events, etc. associated with various different chemical and/or biological processes (e.g., chemical reactions, cell cultures, nucleic acid sequencing). The measurement may detect a constant or variable property, characteristic, or parameter of the substance in the analyte sample 42, such as pH (hydrogen ion concentration/level or activity) in the sample 42, ion concentration/level in the sample 42, or ion concentration/level associated with an enzyme reaction or other type of bioidentifier used for detecting biomolecules. As a specific example, the sensor 10 may be employed for analyte measurements in various processes involving nucleic acids such as DNA. Sensor 10 may also be to sense other types of ions, such as ions of sodium or silver.

The construction of the sensor 10 relocates the sensing area to the backside 12b of the substrate 12, which contrasts with sensors that include frontside sensing areas on a top surface of the BEOL interconnect structure. This relocation of the sensing area eliminates the need for the sensor 10 to also include a sensor gate in a top level wiring layer of the BEOL interconnect structure and hard wiring between this sensor gate and the gate of a frontside transistor. Chip space is freed by the relocation of the sensing area that would otherwise be consumed for this sensing gate. The relocation of the sensing area of sensor 10 also displaces the sensing area from the site of other frontside contacts of the BEOL interconnect structure, which directly isolates the sensing area of sensor 10 receiving the sample 42 from these frontside contacts.

Figure 2:
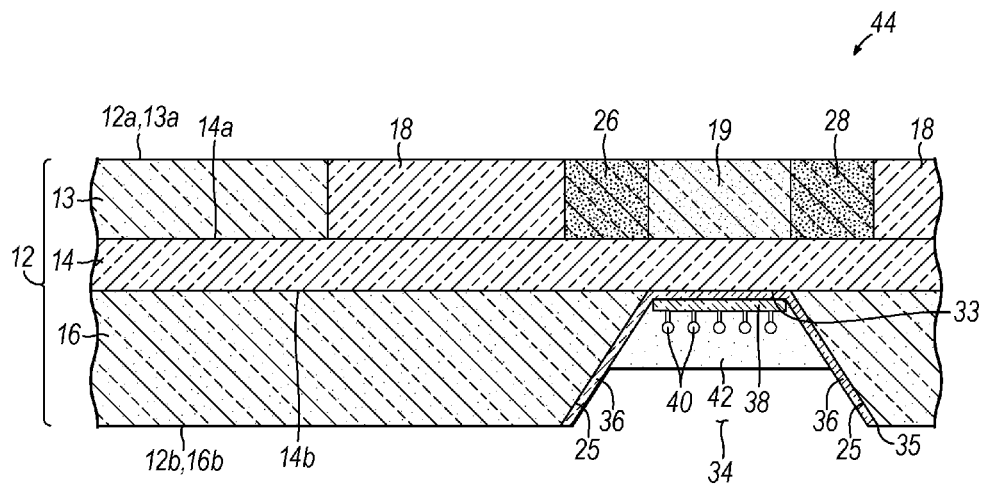

With reference to FIG. 2 and in accordance with an alternative embodiment of the invention, a sensor 44 differs from sensor 10 (FIG. 1) in that the device construction is gate-less. In particular, the dielectric layer 22 and gate electrode 24 are omitted from the device construction of sensor 44. The potential influencing the current between the source 26 and drain 28 originates from the analyte sample 42 contained in the recess 34, and can be directly measured from the analyte sample 42.

Figure 3:
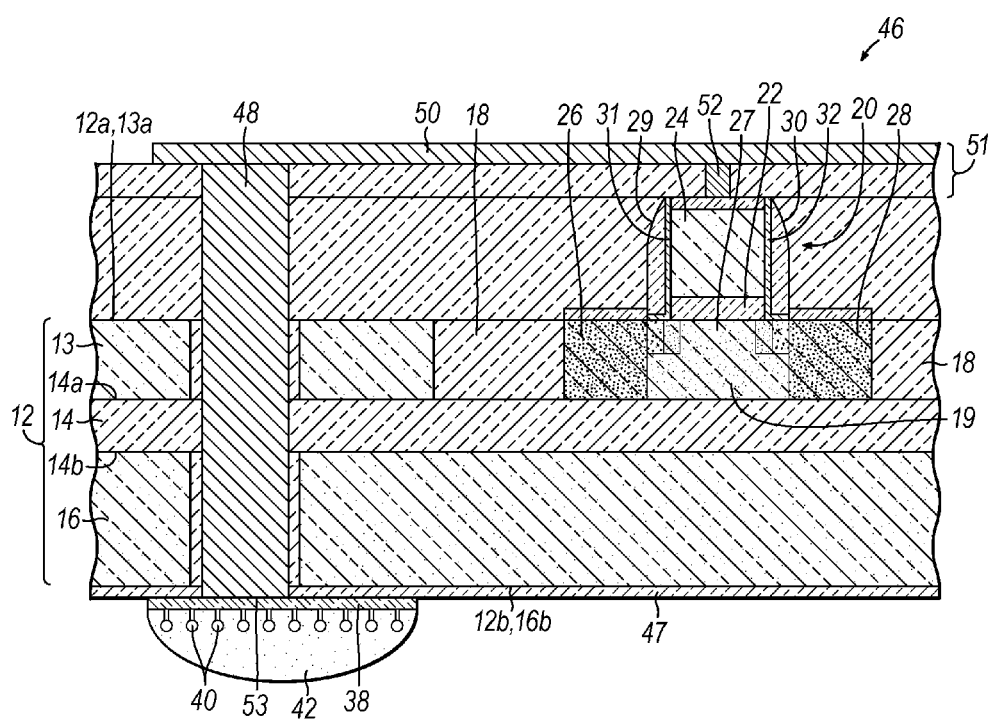

With reference to FIG. 3 and in accordance with an alternative embodiment of the invention, a sensor 46 is formed using a through silicon via (TSV) 48 to provide a connection through the thickness of the substrate 12. The TSV 48 may be fabricated by deep reactive ion etching or laser drilling a deep via into the substrate 12, electrically insulating the deep via, lining the via with a conductive liner that is a diffusion barrier and/or adhesion promoter, and filling the via with a metal (e.g., copper, tungsten). The handle wafer 16 may be thinned from the back side by a recess wet or dry etch to reduce its original thickness and thereby expose the metal of TSV 48. To insulate the backside 12b, an insulating layer 47, such as an oxide, may be deposited and planarized with a chemical mechanical polish (CMP). A metal film may be deposited on the insulating layer 47 and patterned, as described hereinabove, for forming the back-side-metal comprising the sensing layer 38.

The TSV 48 extends from the frontside 12a of thinned substrate 12 through the entire thickness to the backside 12b. When the substrate 12 is thinned as discussed above, an end surface 53 of TSV 48 is exposed. The sensing layer 38 is formed in contact with the end surface 53 of TSV 48 and at the backside 12b of the substrate 12. In one embodiment, the sensing layer 38 directly contacts the end surface 53. A wire 50 and a metal-filled via 52 in a wiring layer of a BEOL interconnect structure 51 on the frontside 12a of substrate 12 may be used to directly connect the TSV 48 and, hence, the sensing layer 38, with the gate electrode 24 of the field effect transistor 20.

The operation of the sensor 46 to detect a property (e.g., ion concentration) of the analyte sample 42 placed on the sensing layer 38 under the control of controller 43 is similar to the operation of sensor 10 (FIG. 1). In the gated construction of this embodiment, the potential influencing the current between the source 26 and drain 28 originates from the analyte sample 42 on the sensing layer 38 and is transferred to the frontside 12a of substrate 12 by the TSV 48 for subsequent transfer to the gate electrode 24. Although a single TSV 48 and sensing layer 38 are provided in the representative embodiment, additional TSVs and sensing layers or multiple TSVs and a single larger sensing layer 38 may be provided and also coupled with the gate electrode 24 of the field effect transistor 20.

In this embodiment, the recess 34 in the handle wafer 16 (FIG. 1) is omitted from the device construction. The backside 12b of substrate 12 is coextensive with the bottom surface 16b of the handle wafer 16. The sensing layer 38 has a planar shape and is in direct contact with the bottom surface 16b.

Figure 4:
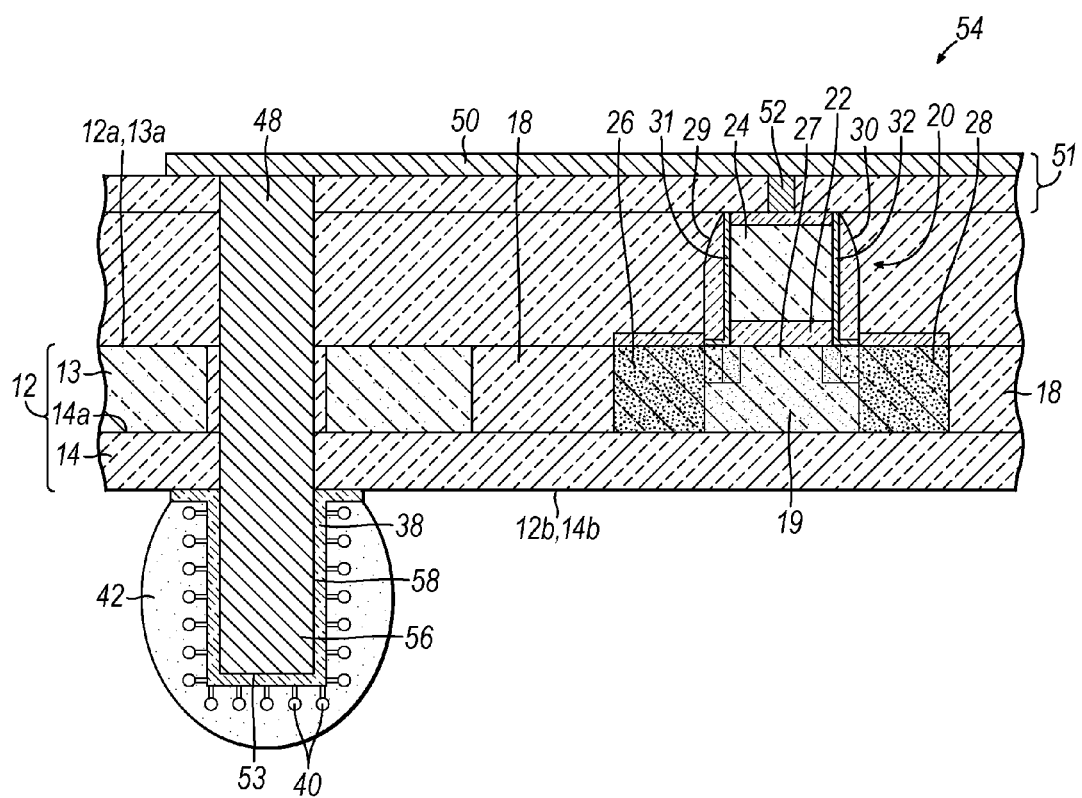

With reference to FIG. 4 and in accordance with an alternative embodiment of the invention, a sensor 54 includes the TSV 48, but the handle wafer 16 is thinned from the backside 12b to completely remove the handle wafer 16. The thinning process may include a wet or dry etch, in addition to grinding and/or polishing, that removes the handle wafer 16 selective to the TSV 48. With the handle wafer 16 removed in its entirety, the tip 56 of the TSV 48 projects from the bottom surface 14b of the buried insulator layer 14 by a given distance that is specified as a design parameter. The distance by which the tip 56 of TSV 48 projects from the surface of the buried insulator layer 14 may be as great as 100 microns (1 m).

The sensing layer 38 at the backside 12b of the substrate 12 is formed on the tip 56 of TSV 48 by depositing and patterning a metal film. The sensing layer 38, which covers the end surface 53 and a sidewall 58 of the tip 56 of TSV 48, is no longer two-dimensional and planar as in the embodiments of FIGS. 1-3 but instead has a three-dimensional, non-planar topography that reproduces the three-dimensional, non-planar geometrical shape of the tip 56 of TSV 48. The recognition element 40 is provided on the sensing layer 38. Because of the three-dimensional geometrical shape, the sensing layer 38 and recognition element 40 are characterized by an increased sensing area compared with a two-dimensional planar configuration. The operation of the sensor 54 under the control of controller 43 to detect a property (e.g., ion concentration) of the analyte sample 42 placed on the sensing layer 38 is as described hereinabove in connection with the operation of sensor 46 (FIG. 3).

In this embodiment, the recess 34 in the handle wafer 16 (FIG. 1) is omitted from the device construction and, instead, the handle wafer 16 may be removed. The backside 12b of substrate 12 is coextensive with the bottom surface 14b of the buried insulator layer 14 and includes the end surface 53 and sidewall 58 of TSV 48.

Figure 5:
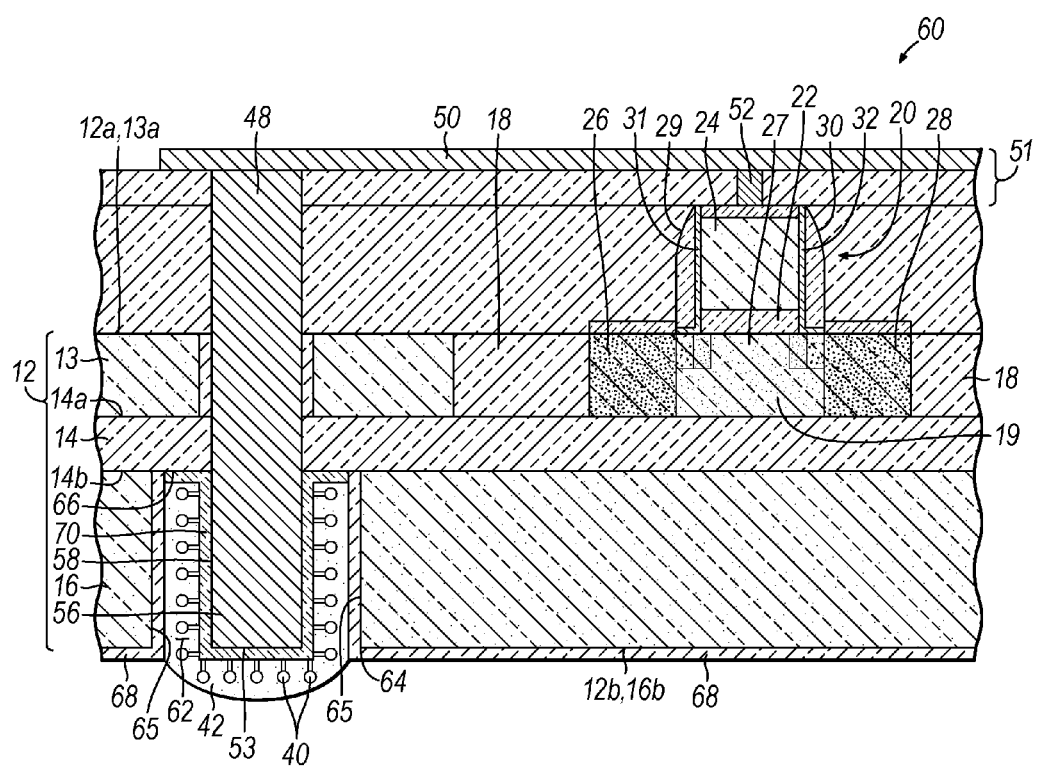

With reference to FIG. 5 and in accordance with an alternative embodiment of the invention, a sensor 60 at the backside 12b of substrate 12 includes the TSV 48, but the handle wafer 16 is thinned without complete removal. A recess, generally indicted by reference numeral 62, is formed in the thinned handle wafer 16 at the backside 12b of the substrate 12. The recess 62 has an unoccluded opening 64 at its mouth, a base surface 66, and a sidewall 65 that connects the opening 64 with the base surface 66. In the representative embodiment, the base surface 66 is coextensive with the buried insulator layer 14. The surrounding relationship of the sidewall 65 relative to the tip 56 of TSV 48 may protect the tip 56 against mechanical damage.

The recess 62 may be defined in the handle wafer 16 using a photolithography process and an etching process as described above with regard to recess 34. The etch chemistry of the etching process may be selected to selectively remove the material of the handle wafer 15 relative to the metal of the TSV 48. The backside 12b of substrate 12 is coextensive with the sidewall 65 and base surface 66 of the recess 62 and the bottom surface 16b of the handle wafer 16.

The tip 56 of the TSV 48 projects from the buried insulator layer 14 and is contained inside of the recess 62. An insulator layer 68, which is similar to insulator layer 36 (FIG. 1), may be applied to the recess 62 as a liner. The insulator layer 68 is absent from the end surface 53 and sidewall 58 of the tip 56 of TSV 48. This can be achieved by patterning the deposited insulator layer 36 with the mask layer used to form the recess 62. A sensing layer 70, which is similar to sensing layer 38 (FIG. 1), is applied and patterned to define a sensing area inside the recess 62 primarily on the end surface 53 and sidewall 58 of the tip 56 of TSV 48 and with a minor portion on the base surface 66. The recognition element 40 is provided on the sensing layer 70. The operation of the sensor 60 under the control of controller 43 to detect a property (e.g., ion concentration) of the analyte sample 42 placed on the sensing layer 38 is as described hereinabove in connection with the operation of sensor 46 (FIG. 3).

Figure 6:
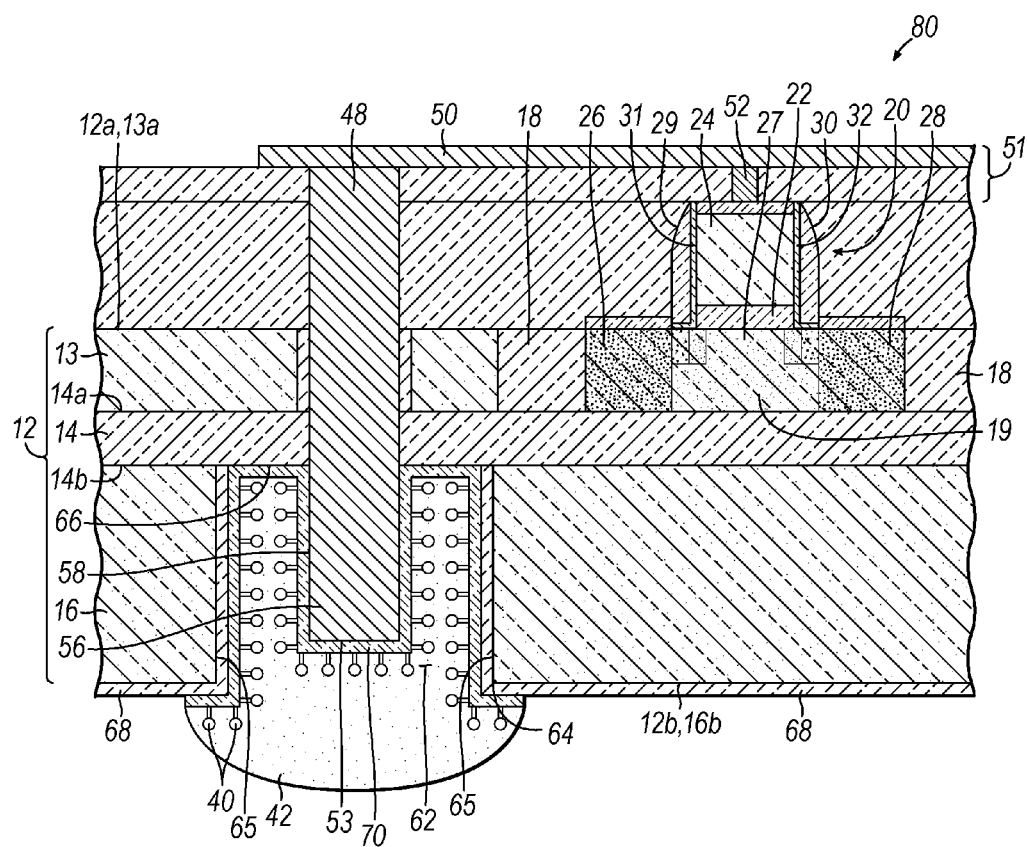

With reference to FIG. 6 and in accordance with an alternative embodiment of the invention, a sensor 80 at the backside 12b of the substrate 12 includes the TSV 48, but the sensing layer 70 is also applied to the sidewall 65 of the recess 62. As shown in the representative embodiment, the sensing layer 70 may also overlap on the insulator layer 68. This arrangement further increases the area on which the recognition element 40 can be applied. The operation of the sensor 80 under the control of controller 43 to detect a property (e.g., ion concentration) of the analyte sample 42 placed on the sensing layer 38 is as described hereinabove in connection with the operation of sensor 46 (FIG. 3).

The various embodiments of the sensor disclosed herein may be replicated to provide a large number of such sensors arranged in an array and configured to monitor one or more independent chemical reactions or events occurring in proximity to each individual sensor of the array. An apparatus may be used to deliver analyte samples to the sensors and to clean the sensors by removing the analyte samples between measurements.

Figure 7:
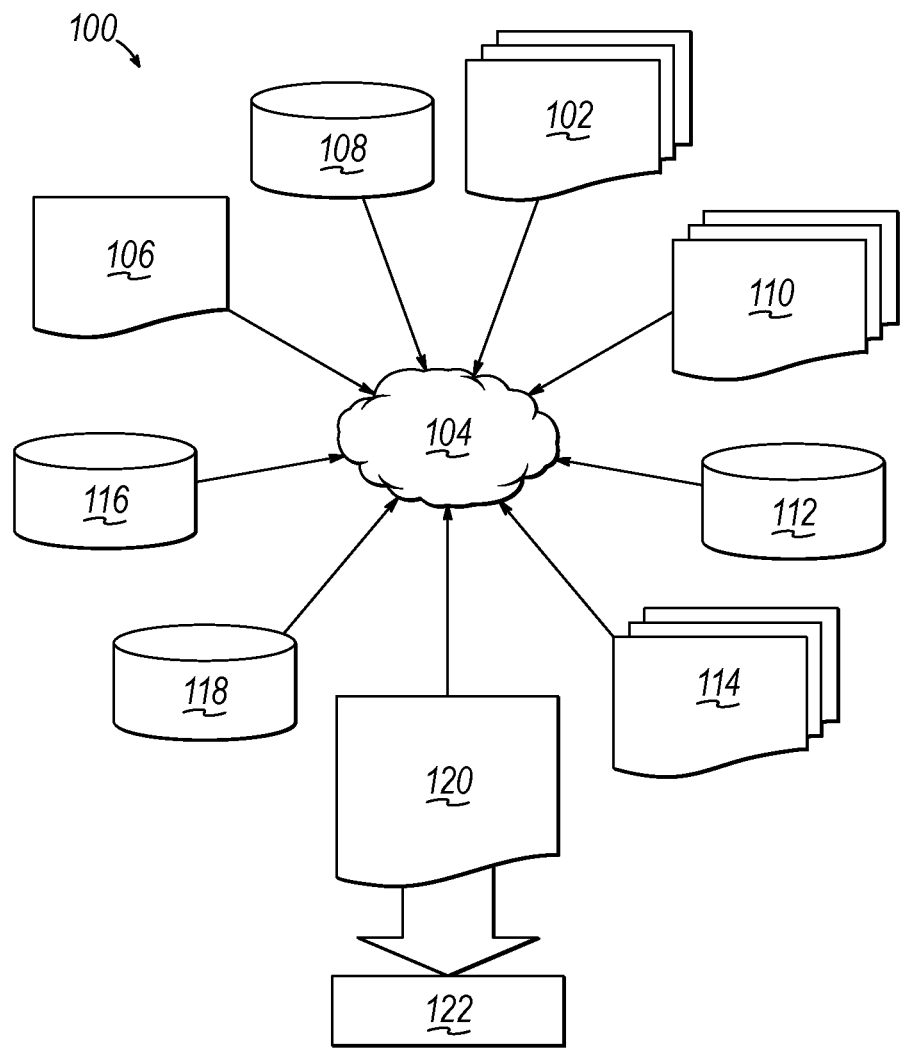
FIG. 7 is a flow diagram of a design process used in semiconductor design, manufacture, and/or test.

FIG. 7 shows a block diagram of an exemplary design flow 100 used for example, in semiconductor IC logic design, simulation, test, layout, and manufacture. Design flow 100 includes processes, machines and/or mechanisms for processing design structures or devices to generate logically or otherwise functionally equivalent representations of the design structures and/or devices described above and shown in FIG. 1-6. The design structures processed and/or generated by design flow 100 may be encoded on machine-readable transmission or storage media to include data and/or instructions that when executed or otherwise processed on a data processing system generate a logically, structurally, mechanically, or otherwise functionally equivalent representation of hardware components, circuits, devices, or systems. Machines include, but are not limited to, any machine used in an IC design process, such as designing, manufacturing, or simulating a circuit, component, device, or system. For example, machines may include: lithography machines, machines and/or equipment for generating masks (e.g. e-beam writers), computers or equipment for simulating design structures, any apparatus used in the manufacturing or test process, or any machines for programming functionally equivalent representations of the design structures into any medium (e.g. a machine for programming a programmable gate array).

Design flow 100 may vary depending on the type of representation being designed. For example, a design flow 100 for building an application specific IC (ASIC) may differ from a design flow 100 for designing a standard component or from a design flow 100 for instantiating the design into a programmable array, for example a programmable gate array (PGA) or a field programmable gate array (FPGA) offered by Altera® Inc. or Xilinx® Inc.

FIG. 7 illustrates multiple such design structures including an input design structure 102 that is preferably processed by a design process 104. Design structure 102 may be a logical simulation design structure generated and processed by design process 104 to produce a logically equivalent functional representation of a hardware device. Design structure 102 may also or alternatively comprise data and/or program instructions that when processed by design process 104, generate a functional representation of the physical structure of a hardware device. Whether representing functional and/or structural design features, design structure 102 may be generated using electronic computer-aided design (ECAD) such as implemented by a core developer/designer. When encoded on a machine-readable data transmission, gate array, or storage medium, design structure 102 may be accessed and processed by one or more hardware and/or software modules within design process 104 to simulate or otherwise functionally represent an electronic component, circuit, electronic or logic module, apparatus, device, or system such as those shown in FIG. 1-6. As such, design structure 102 may comprise files or other data structures including human and/or machine-readable source code, compiled structures, and computer-executable code structures that when processed by a design or simulation data processing system, functionally simulate or otherwise represent circuits or other levels of hardware logic design. Such data structures may include hardware-description language (HDL) design entities or other data structures conforming to and/or compatible with lower-level HDL design languages such as Verilog and VHDL, and/or higher level design languages such as C or C++.

Design process 104 preferably employs and incorporates hardware and/or software modules for synthesizing, translating, or otherwise processing a design/simulation functional equivalent of the components, circuits, devices, or logic structures shown in FIG. 1-6 to generate a netlist 106 which may contain design structures such as design structure 102. Netlist 106 may comprise, for example, compiled or otherwise processed data structures representing a list of wires, discrete components, logic gates, control circuits, I/O devices, models, etc. that describes the connections to other elements and circuits in an integrated circuit design. Netlist 106 may be synthesized using an iterative process in which netlist 106 is resynthesized one or more times depending on design specifications and parameters for the device. As with other design structure types described herein, netlist 106 may be recorded on a machine-readable data storage medium or programmed into a programmable gate array. The medium may be a non-volatile storage medium such as a magnetic or optical disk drive, a programmable gate array, a compact flash, or other flash memory. Additionally, or in the alternative, the medium may be a system or cache memory, buffer space, or electrically or optically conductive devices and materials on which data packets may be transmitted and intermediately stored via the Internet, or other networking suitable means.

Design process 104 may include hardware and software modules for processing a variety of input data structure types including netlist 106. Such data structure types may reside, for example, within library elements 108 and include a set of commonly used elements, circuits, and devices, including models, layouts, and symbolic representations, for a given manufacturing technology (e.g., different technology nodes, 32 nm, 45 nm, 90 nm, etc.). The data structure types may further include design specifications 110, characterization data 112, verification data 114, design rules 116, and test data files 118 which may include input test patterns, output test results, and other testing information. Design process 104 may further include, for example, standard mechanical design processes such as stress analysis, thermal analysis, mechanical event simulation, process simulation for operations such as casting, molding, and die press forming, etc. One of ordinary skill in the art of mechanical design can appreciate the extent of possible mechanical design tools and applications used in design process 104 without deviating from the scope and spirit of the invention. Design process 104 may also include modules for performing standard circuit design processes such as timing analysis, verification, design rule checking, place and route operations, etc.

Design process 104 employs and incorporates logic and physical design tools such as HDL compilers and simulation model build tools to process design structure 102 together with some or all of the depicted supporting data structures along with any additional mechanical design or data (if applicable), to generate a second design structure 120. Design structure 120 resides on a storage medium or programmable gate array in a data format used for the exchange of data of mechanical devices and structures (e.g. information stored in an IGES, DXF, Parasolid XT, JT, DRG, or any other suitable format for storing or rendering such mechanical design structures). Similar to design structure 102, design structure 120 preferably comprises one or more files, data structures, or other computer-encoded data or instructions that reside on transmission or data storage media and that when processed by an ECAD system generate a logically or otherwise functionally equivalent form of one or more of the embodiments of the invention shown in FIG. 1-6. In one embodiment, design structure 120 may comprise a compiled, executable HDL simulation model that functionally simulates the devices shown in FIG. 1-6.

Design structure 120 may also employ a data format used for the exchange of layout data of integrated circuits and/or symbolic data format (e.g. information stored in a GDSII (GDS2), GL1, OASIS, map files, or any other suitable format for storing such design data structures). Design structure 120 may comprise information such as, for example, symbolic data, map files, test data files, design content files, manufacturing data, layout parameters, wires, levels of metal, vias, shapes, data for routing through the manufacturing line, and any other data required by a manufacturer or other designer/developer to produce a device or structure as described above and shown in FIG. 1-6. Design structure 120 may then proceed to a stage 122 where, for example, design structure 120: proceeds to tape-out, is released to manufacturing, is released to a mask house, is sent to another design house, is sent back to the customer, etc.

The method as described above is used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

It will be understood that when an element is described as being "connected" or "coupled" to or with another element, it can be directly connected or coupled to the other element or, instead, one or more intervening elements may be present. In contrast, when an element is described as being "directly connected" or "directly coupled" to another element, there are no intervening elements present. When an element is described as being "indirectly connected" or "indirectly coupled" to another element, there is at least one intervening element present.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of forming a sensor used to detect a property of a substance, the method comprising:
    forming a drain and a source of a field effect transistor at a frontside of a substrate;
    forming a sensing layer that is configured to receive the substance and that is located at a backside of the substrate opposite from the frontside of the substrate; and
    forming a through silicon via (TSV) extending through the substrate and coupling the sensing layer with the field effect transistor,
    wherein the TSV has a tip that projects outwardly from the backside of the substrate, and the sensing layer is formed at least partially on the tip of the TSV.

2. The method of claim 1 further comprising:
    forming a recess at the backside of the substrate,
    wherein the sensing layer is formed at least partially on the substrate in the recess.

3. The method of claim 2 further comprising;
    forming a gate electrode of the field effect transistor at the frontside of the substrate.

4. The method of claim 3 wherein the TSV couples the sensing layer on the backside of the substrate with the gate electrode on the frontside of the substrate.

5. The method of claim 2 wherein the substrate is a semiconductor-on-insulator (SOI) wafer, the recess exposes a buried dielectric layer of the SOI wafer, and the sensing layer is at least partially positioned on the buried dielectric layer exposed by the recess.

6. The method of claim 5 wherein the drain and the source of the field effect transistor are formed in a device layer of the SOI wafer.

7. The method of claim 1 further comprising:
    forming a gate electrode of the field effect transistor at the frontside of the substrate.

8. The method of claim 7 wherein the TSV couples the sensing layer on the backside of the substrate with the gate electrode on the frontside of the substrate.

9. The method of claim 1 further comprising:
    forming a recess at the backside of the substrate,
    wherein the tip of the TSV is positioned in the recess.

10. The method of claim 9 further comprising:
    forming a portion of the sensing layer on a sidewall of the recess.

11. A device structure for a sensor used to detect a property of a substance, the device structure formed using a substrate having a frontside and a backside opposite from the frontside, and the device structure comprising:
    a field effect transistor including a drain and a source at the frontside of the substrate;
    a sensing layer located at the backside of the substrate, the sensing layer configured to receive the substance; and
    a through silicon via (TSV) extending through the substrate and coupling the sensing layer with the field effect transistor,
    wherein the TSV has a tip that projects outwardly from the backside of the substrate, and the sensing layer is positioned at least partially on the tip of the TSV.

12. The device structure of claim 11 further comprising:
    a recess at the backside of the substrate,
    wherein the sensing layer is located at least partially on the substrate in the recess.

13. The device structure of claim 12 further comprising;
    a gate electrode of the field effect transistor at the frontside of the substrate.

14. The device structure of claim 13 the TSV couples the sensing layer at the backside of the substrate with the gate electrode at the frontside of the substrate.

15. The device structure of claim 12 wherein the substrate used to form the device structure is a semiconductor-on-insulator (SOI) wafer, the recess exposes a buried dielectric layer of the SOI wafer, and the sensing layer is positioned at least partially on the buried dielectric layer exposed by the recess.

16. The device structure of claim 15 wherein the drain and the source of the field effect transistor are formed in a device layer of the SOI wafer.

17. The device structure of claim 11 wherein the field effect transistor further includes a gate electrode at the frontside of the substrate.

18. The device structure of claim 17 wherein the TSV couples the sensing layer on the backside of the substrate with the gate electrode on the frontside of the substrate.

19. The device structure of claim 11, wherein the substrate used to form the device structure is a semiconductor-on-insulator (SOI) wafer including a buried dielectric layer, and the tip projects from the buried dielectric layer outwardly from the backside of the substrate.

20. The device structure of claim 11 further comprising:
    a recess at the backside of the substrate,
    wherein the tip of the TSV is positioned in the recess.

21. The device structure of claim 20 wherein the substrate is a semiconductor-on-insulator (SOI) wafer including a buried dielectric layer and a handle wafer, the recess extends through the handle wafer to the buried dielectric layer, and the tip projects from the buried dielectric layer outwardly from the backside of the substrate.

22. The device structure of claim 21 wherein the recess includes a sidewall, and the sensing layer is at least partially positioned on the sidewall of the recess.

23. A hardware description language (HDL) design structure encoded on a machine-readable data storage medium, the HDL design structure comprising elements that when processed in a computer-aided design system generates a machine-executable representation of a sensor used to detect a property of a substance, the HDL design structure comprising:
    a field effect transistor including a drain and a source at the frontside of the substrate;
    a sensing layer located at the backside of the substrate, the sensing layer configured to receive the substance; and a through silicon via (TSV) extending through the substrate and coupling the sensing layer with the field effect transistor, wherein the TSV has a tip that projects outwardly from the backside of the substrate, and the sensing layer is positioned at least partially on the tip of the TSV.

24. The HDL design structure of claim 23 wherein the HDL design structure comprises a netlist.

25. The HDL design structure of claim 23 wherein the DHL design structure resides on storage medium as a data format used for the exchange of layout data of integrated circuits.

26. The HDL design structure of claim 23 wherein the HDL design structure resides in a programmable gate array.

* * * * *